(12) United States Patent
Moore et al.

(10) Patent No.: US 12,053,205 B2
(45) Date of Patent: Aug. 6, 2024

(54) METHOD AND SYSTEM FOR PROVIDING ACTIVE TISSUE SITE DEBRIDEMENT

(71) Applicant: Solventum Intellectual Properties Company, Maplewood, MN (US)

(72) Inventors: Brett L. Moore, San Antonio, TX (US); Christopher A. Carroll, San Antonio, TX (US); Justin R. Rice, San Antonio, TX (US); Benjamin A. Pratt, Wimborne (GB); James Seddon, Wimborne (GB)

(73) Assignee: Solventum Intellectual Properties Company, Maplewoord, MN (US)

( * ) Notice: Subject to any disclaimer, the term of this patent is extended or adjusted under 35 U.S.C. 154(b) by 902 days.

(21) Appl. No.: 17/057,821

(22) PCT Filed: May 23, 2019

(86) PCT No.: PCT/US2019/033749
§ 371 (c)(1),
(2) Date: Nov. 23, 2020

(87) PCT Pub. No.: WO2019/226892
PCT Pub. Date: Nov. 28, 2019

(65) Prior Publication Data
US 2021/0196310 A1    Jul. 1, 2021

Related U.S. Application Data

(60) Provisional application No. 62/676,561, filed on May 25, 2018.

(51) Int. Cl.
*A61B 17/3207* (2006.01)
*A61B 17/00* (2006.01)
(Continued)

(52) U.S. Cl.
CPC .......... *A61B 17/320758* (2013.01); *A61B 2017/00017* (2013.01); *A61B 2017/00761* (2013.01);
(Continued)

(58) Field of Classification Search
CPC ......... A61B 2017/00761; A61B 2017/320004; A61B 2017/320008; A61F 13/00008;
(Continued)

(56) References Cited

U.S. PATENT DOCUMENTS 1,355,846 A   10/1920   Rannells
2,547,758 A    4/1951   Keeling
(Continued)

FOREIGN PATENT DOCUMENTS

AU   550575 B2    3/1986
AU   755496 B2   12/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Martin T Ton

(57) ABSTRACT

A wound debridement system includes a wound dressing having an active layer and a wound interface layer. The active layer is formed from one or more drive elements arranged about a film layer, by which the drive elements are attached to the wound interface layer. Activation of the drive elements is configured to cause the movement of the wound interface layer relative to a tissue site to which the wound dressing is applied. The drive elements may include one or more drive members formed of a material having a shape
(Continued)

memory effect configured to transition the drive members between expanded and collapsed configurations and/or one or more motors configured to translate or oscillate the active layer. The wound interface layer may be formed having an abrasive wound-facing surface, such that the movement of the wound interface layer causes a mechanical disruption and debridement of debris at the tissue site.

10 Claims, 5 Drawing Sheets

(51) Int. Cl.
*A61B 17/32* (2006.01)
*A61M 1/00* (2006.01)

(52) U.S. Cl.
CPC ............... *A61B 2017/00867* (2013.01); *A61B 2017/320004* (2013.01); *A61M 1/90* (2021.05)

(58) Field of Classification Search
CPC .......... A61F 13/00021; A61F 13/00029; A61F 13/00034; A61F 2013/0028; A61M 1/90
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0236269 A1* | 11/2004 | Marchitto ............. A61M 37/00 604/22 |
| 2007/0239078 A1* | 10/2007 | Jaeb ........................ A61N 7/00 601/2 |
| 2010/0160871 A1* | 6/2010 | Seegert ............. A61K 38/4886 604/290 |
| 2012/0172779 A1* | 7/2012 | Spinelli ............... A61F 13/0243 602/53 |
| 2015/0320603 A1* | 11/2015 | Locke ................ A61B 17/3205 604/543 |
| 2015/0366719 A1* | 12/2015 | Levinson ............ A61F 13/0233 606/167 |

FOREIGN PATENT DOCUMENTS

| | | |
|---|---|---|
| CA | 2005436 A1 | 6/1990 |
| DE | 2640413 A1 | 3/1978 |
| DE | 4306478 A1 | 9/1994 |
| DE | 29504378 U1 | 9/1995 |
| EP | 0100148 A1 | 2/1984 |
| EP | 0117632 A2 | 9/1984 |
| EP | 161865 A2 | 11/1985 |
| EP | 358302 A2 | 3/1990 |
| EP | 1018967 A1 | 7/2000 |

(56) References Cited

FOREIGN PATENT DOCUMENTS

| GB | 2197789 A | 6/1988 |
|---|---|---|
| GB | 2220357 A | 1/1990 |
| GB | 2235877 A | 3/1991 |
| GB | 2329127 A | 3/1999 |
| GB | 2333965 A | 8/1999 |
| JP | 4129536 B2 | 8/2008 |
| WO | 80/02182 A1 | 10/1980 |
| WO | 90010424 A1 | 9/1990 |
| WO | 93009727 A1 | 5/1993 |
| WO | 94020041 A1 | 9/1994 |
| WO | 9605873 A1 | 2/1996 |
| WO | 97/18007 A1 | 5/1997 |
| WO | 9913793 A1 | 3/1999 |
| WO | WO-2013/066694 A2 | 5/2013 |
| WO | WO-2018/005449 A1 | 1/2018 |

OTHER PUBLICATIONS

Chariker, Mark E., M.D., et al; "Effective Management of incisional and cutaneous fistulae with closed suction wound drainage"; Contemporary Surgery, vol. 34, Jun. 1989, pp. 59-63.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A.C.® Therapy Clinical Guidelines: A Reference Source for Clinicians; Jul. 2007.
International Search Report and Written Opinion in International Application No. PCT/US2019/033749, mailed on Oct. 16, 2019.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/the British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

\* cited by examiner

METHOD AND SYSTEM FOR PROVIDING ACTIVE TISSUE SITE DEBRIDEMENT

CROSS-REFERENCE TO RELATED APPLICATIONS

This Application claims the benefit of priority to international patent application number PCT/US2019/033749, filed on May 23, 2019, which claims the benefit of priority to U.S. Provisional Application No. 62/676,561, filed on May 25, 2018, the complete disclosures of which are hereby incorporated herein by reference in their entireties.

BACKGROUND

The present disclosure relates generally to tissue treatment systems, and more particularly, but without limitation, to a wound debridement system for active disruption and/or debridement of non-viable tissue at a tissue site without continual user intervention.

During treatment of a tissue site, such as, e.g. a wound site, debris may develop on or in the tissue site. In various embodiments, the debris may include biofilms, necrotic tissue, foreign bodies, eschar, lacerated tissue, devitalized tissue, contaminated tissue, damaged tissue, infected tissue, exudate, highly viscous exudate, fibrinous slough and/or other material. The debris may cover all or a portion of the tissue site.

The presence of debris in, on, or surrounding a tissue site may cause numerous problems. For example, debris that covers the tissue site may impair healing of the tissue site. Debris can also lower the effectiveness of beneficial tissue site treatments by preventing the treatments from reaching the tissue site. The presence of debris may also increase healing times and the risk of a more serious infection. Accordingly, in various embodiments, it may be desirable to disrupt the debris at a tissue site.

SUMMARY

One implementation of the present disclosure is an active debridement wound dressing including a wound interface layer and an active layer. The wound interface layer includes an abrasive surface configured to contact a wound and mechanically debride the wound when the wound interface layer moves relative to the wound. The active layer is coupled to the wound interface layer and includes a shape memory alloy configured to expand or contract when activated, thereby causing the wound interface layer to move relative to the wound and mechanically debride the wound.

In some embodiments, the active layer includes a fenestrated film fixed to the wound interface layer. The shape memory alloy includes a plurality of segments of the shape memory alloy fixed to the fenestrated film. The active layer includes a central hub of the shape memory alloy and a plurality of radial segments of the shape memory alloy extending radially outward from the central hub. The shape memory alloy may also extend about the perimeter of the active layer and may form a closed shape around the central hub and the plurality of radial segments. The plurality of radial segments may connect the central hub to the perimeter.

In some embodiments, the shape memory alloy is activated by electric current and is configured to expand or contact when the electric current is applied to the shape memory alloy. In other embodiments, the shape memory alloy is activated by light and expands or contracts when one or more wavelengths of light are applied to the shape memory alloy.

In yet other embodiments, the shape memory alloy is activated by temperature and is configured to expand or contact when a temperature of the shape memory alloy reaches an activation temperature. In some embodiments, the activation temperature is between a room temperature and a body temperature such that the shape memory alloy is activated by body heat. The room temperature is between 65° F. and 75° F. and the body temperature is between 97° F. and 100° F.

In some embodiments, the activation temperature is between a body temperature and a temperature of a fluid delivered to the wound dressing such that the shape memory alloy is activated when the fluid is delivered to the wound dressing. In some embodiments, the temperature of the fluid delivered to the wound dressing and the activation temperature of the shape memory alloy are less than the body temperature. In other embodiments, the temperature of the fluid delivered to the wound dressing and the activation temperature of the shape memory alloy are greater than the body temperature. The fluid delivered to the wound dressing is a warm or cool saline solution.

In some embodiments, a foam layer is coupled to the active layer opposite the wound interface layer such that the active layer is encapsulated between the foam layer and the wound interface layer.

In some embodiments, a control unit is coupled to the active layer and is configured to activate the active layer by applying at least one of an electric current, a temperature, or light to the active layer. The control unit is configured to communicate with a driver unit outside the wound dressing and to activate the active layer upon receiving a control signal from the driver unit.

In some embodiments, the shape memory alloy is configured to forcefully return to a non-activated size or shape when no longer activated. The shape memory alloy is configured to oscillate between the non-activated size or shape and an activated size or shape to impart oscillating movement to the wound interface layer. In some embodiments, a drape layer sealable to a patient's skin surrounds the wound and is configured to maintain the wound at negative pressure.

One implementation of the present disclosure is an active debridement wound dressing including a wound interface layer and an active layer. The wound interface layer includes an abrasive surface configured to contact a wound and mechanically debride the wound when the wound interface layer moves relative to the wound. The active layer is coupled to the wound interface layer and includes an electro-active polymer configured to expand or contract when activated, thereby causing the wound interface layer to move relative to the wound and mechanically debride the wound.

In some embodiments, the active layer includes a fenestrated film fixed to the wound interface layer; and the electro-active polymer includes a plurality of segments of the electro-active polymer fixed to the fenestrated film.

In some embodiments, the active layer includes a central hub of the electro-active polymer and a plurality of radial segments of the electro-active polymer extending radially outward from the central hub. The active layer includes an electro-active polymer extending about the perimeter of the active layer and forming a closed shape around the central hub and the plurality of radial segments. The plurality of radial segments connect the central hub to the perimeter. In some embodiments, the electro-active polymer is activated by electric current and configured to expand or contact when the electric current is applied to the electro-active polymer.

In some embodiments, a foam layer is coupled to the active layer opposite the wound interface layer such that the active layer is encapsulated between the foam layer and the wound interface layer. A control unit is coupled to the active layer and is configured to activate the active layer by applying an electric current to the active layer. The control unit is configured to communicate with a driver unit outside the wound dressing and to activate the active layer upon receiving a control signal from the driver unit.

In some embodiments, the electro-active polymer is configured to forcefully return to a non-activated size or shape when no longer activated. In some embodiments, the electro-active polymer is configured to oscillate between the non-activated size or shape and an activated size or shape to impart oscillating movement to the wound interface layer. In some embodiments, a drape layer is sealable to a patient's skin surrounding the wound and is configured to maintain the wound at negative pressure.

In one implementation in of the disclosure, an active debridement wound dressing includes a wound interface layer and an active layer. The wound interface layer includes an abrasive surface configured to contact a wound and mechanically debride the wound when the wound interface layer moves relative to the wound. The active layer is coupled to the wound interface layer and includes one or more oscillating motors configured to cause the wound interface layer to move relative to the wound when activated and thereby mechanically debride the wound. In some embodiments, the active layer includes a fenestrated film fixed to the wound interface layer; and the one or more oscillating motors are fixed to the fenestrated film.

In some embodiments, the one or more oscillating motors are by powered by electric current and are configured to cause the wound interface layer to move as the electric current is applied to the one or more oscillating motors. A foam layer may be coupled to the active layer opposite the wound interface layer such that the active layer is encapsulated between the foam layer and the wound interface layer. A control unit may be coupled to the one or more oscillating motors and may be configured to drive the one or more oscillating motors by applying an electric current to the one or more oscillating motors. The control unit may be configured to communicate with a driver unit outside the wound dressing and to drive the one or more oscillating motors upon receiving a control signal from the driver unit. In some embodiments, the control unit is configured to drive the one or more oscillating motors in response to a change in pressure within the wound dressing. In some embodiments, a drape layer is sealable to a patient's skin surrounding the wound and is configured to maintain the wound at negative pressure.

In one implementation of the present disclosure, an active debridement wound therapy system includes a therapy unit and a wound dressing. The wound dressing includes a wound interface layer and an active layer. The wound interface layer includes an abrasive surface configured to contact a wound and mechanically debride the wound when the wound interface layer moves relative to the wound. The active layer is coupled to the wound interface layer and is configured to cause the wound interface layer to move relative to the wound when activated and thereby mechanically debride the wound. The therapy unit is separate from the wound dressing and is configured to activate and deactivate the active layer.

In some embodiments, the therapy unit includes a driver unit configured to activate the active layer by applying at least one of an electric current, a temperature, or light to the active layer. In some embodiments, the wound dressing includes a control unit coupled to the active layer and configured to communicate with the therapy unit. The control unit is configured to activate the active layer upon receiving a control signal from the therapy unit.

In some embodiments, the active layer includes a shape memory alloy configured to expand or contract when activated, thereby causing the wound interface layer to move relative to the wound and mechanically debride the wound. In some embodiments, the active layer includes a fenestrated film fixed to the wound interface layer. The shape memory alloy includes a plurality of segments of the shape memory alloy fixed to the fenestrated film. The active layer includes a central hub of the shape memory alloy and a plurality of radial segments of the shape memory alloy extending radially outward from the central hub. The active layer may further be defined in that the shape memory alloy forms extends about the perimeter of the active layer and may form a closed shape around the central hub and the plurality of radial segments. The plurality of radial segments may connect the central hub to the perimeter.

In some embodiments, the shape memory alloy is activated by electric current and is configured to expand or contact when the electric current is applied to the shape memory alloy. In other embodiments, the shape memory alloy is activated by light and expands or contacts when one or more wavelengths of light are applied to the shape memory alloy.

In yet other embodiments, the shape memory alloy is activated by temperature and is configured to expand or contact when a temperature of the shape memory alloy reaches an activation temperature. The activation temperature is between a room temperature and a body temperature such that the shape memory alloy is activated by body heat. The room temperature is between 65° F. and 75° F. and the body temperature is between 97° F. and 100° F.

In some embodiments, the activation temperature is between a body temperature and a temperature of a fluid delivered to the wound dressing such that the shape memory alloy is activated when the fluid is delivered to the wound dressing. In some embodiments, the temperature of the fluid delivered to the wound dressing and the activation temperature of the shape memory alloy are less than the body temperature. In other embodiments, the temperature of the fluid delivered to the wound dressing and the activation temperature of the shape memory alloy are greater than the body temperature. The fluid delivered to the wound dressing is a warm or cool saline solution.

In some embodiments, the active layer includes an electro-active polymer configured to expand or contract when activated, thereby causing the wound interface layer to move relative to the wound and mechanically debride the wound. In some embodiments, the active layer includes a fenestrated film fixed to the wound interface layer; and the electro-active polymer includes a plurality of segments of the electro-active polymer fixed to the fenestrated film.

In some embodiments, the active layer includes a central hub of the electro-active polymer and a plurality of radial segments of the electro-active polymer extending radially outward from the central hub. The active layer includes an electro-active polymer extending about the perimeter of the active layer and forming a closed shape around the central hub and the plurality of radial segments. The plurality of radial segments connect the central hub to the perimeter. In some embodiments, the electro-active polymer is activated by electric current and configured to expand or contact when the electric current is applied to the electro-active polymer.

In some embodiments, the active layer includes one or more oscillating motors configured to cause the wound interface layer to move relative to the wound when activated and thereby mechanically debride the wound. In some embodiments, the active layer includes a fenestrated film fixed to the wound interface layer and the one or more oscillating motors are fixed to the fenestrated film. In some embodiments, the one or more oscillating motors are by powered by electric current and are configured to cause the wound interface layer to move the electric current is applied to the one or more oscillating motors.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Referring to FIGS. 1-5, various embodiments of an active wound debridement system 1 configured to disrupt areas of debris 7 at a tissue site 5, such as, e.g. a wound site, are shown. The active wound debridement system 1 is configured to provide continued, active mechanical debridement of debris 7 at the tissue site 5 without requiring any additional user skill or effort to operate the wound debridement system 1 than would be required to apply and activate an existing negative pressure wound therapy ("NPWT") system, such as e.g. a V.A.C.® therapy unit as available from Kinetic Concepts, Inc. (KCI) of San Antonio, Tex.

Figure 1:
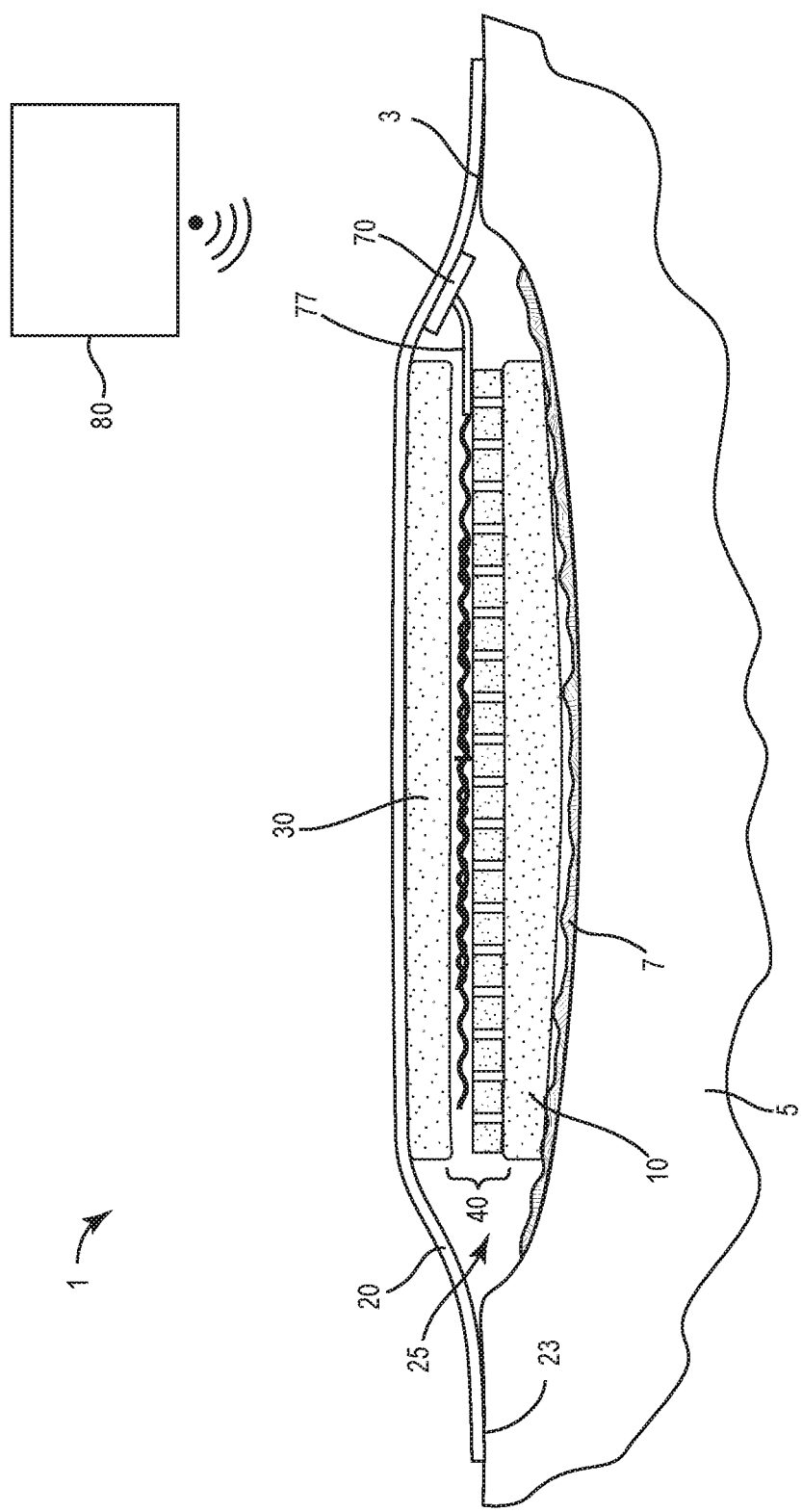
FIG. 1 is a cross-sectional side view of an active wound debridement system applied to a tissue site, according to an exemplary embodiment.
Figure 5:
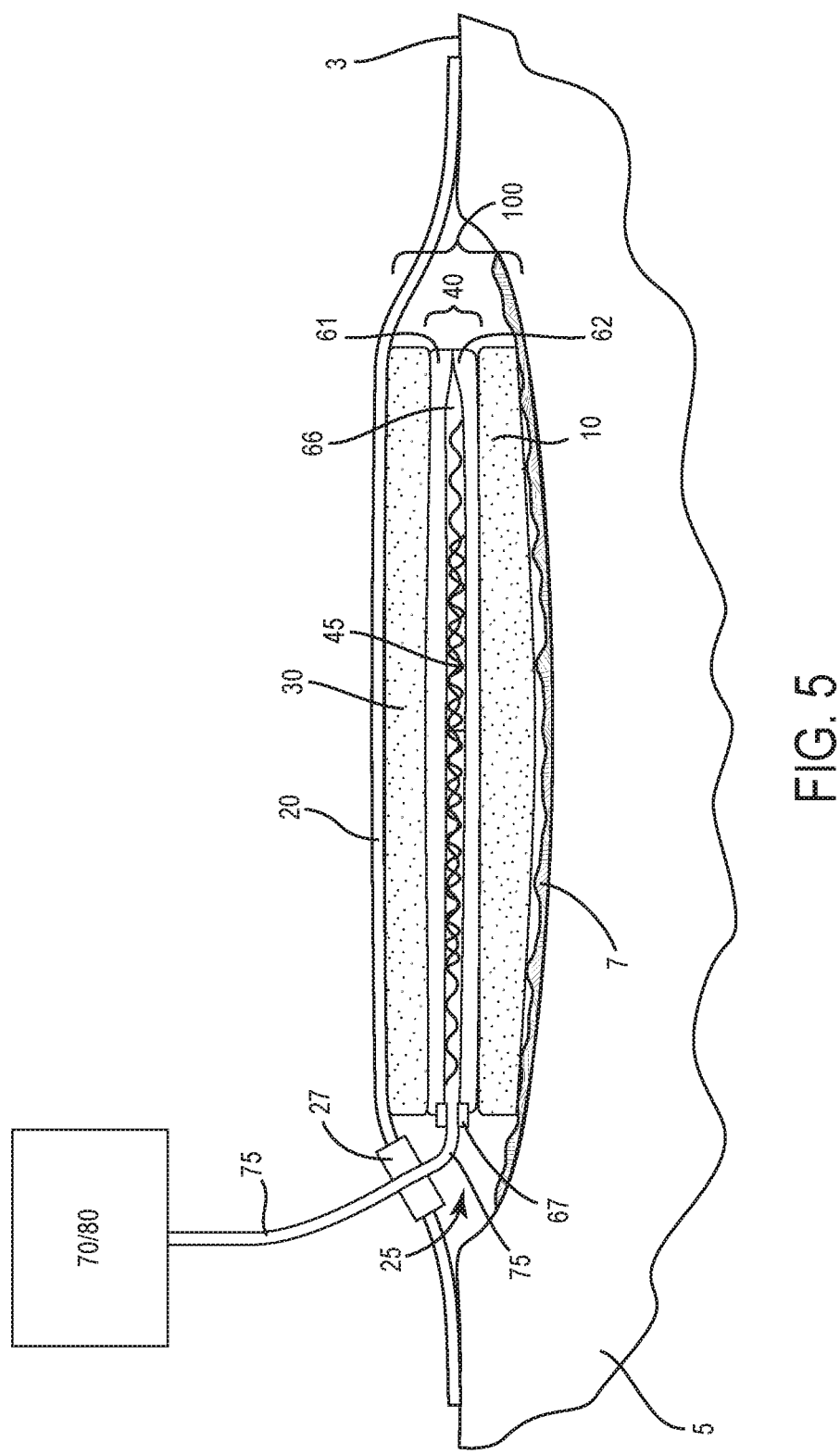
FIG. 5 is a cross-sectional side view of an active wound debridement system applied to a tissue site, according to an exemplary embodiment.

As shown in FIGS. 1 and 5, the wound debridement system 1 generally comprises an active debridement wound dressing 100, a drape layer 20 configured to position the wound dressing 100 at a desired tissue site 5, a drive unit 70 adapted to activate the active layer 40, and a control unit 80 configured to control the activation of the active layer 40 by the drive unit 70.

During operation of the wound debridement system 1, the wound dressing 100 is positioned on or within a desired tissue site 5. Once positioned, the wound dressing 100 is secured to the patient's skin 3 using the drape layer 20. In some embodiments, the drape layer 20 may be applied to the patient's skin 3 so as to form a sealed, substantially fluid-tight treatment space 25 surrounding the tissue site 5 and the wound dressing 100.

The control unit 80 may be operated to control the activation of the active layer 40. In some embodiments, the control unit 80 may be adapted to control the activation of the active layer 40 via a drive unit 70. The activation of the active layer 40 drives the wound interface layer 10 such that the wound interface layer 10 is translated laterally and/or longitudinally relative to the tissue site 5 (e.g. in a plane substantially parallel to a plane of the wound bed or along a contour configured to follow a contour of the wound bed). This movement of the wound interface layer 10 laterally and/or longitudinally relative to the tissue site 5 acts to mechanically disrupt and debride debris 7 located at the tissue site 5.

In some embodiments, the wound debridement system 1 may be used in conjunction with, or form a part of, an additional therapeutic treatment system configured to provide additional therapeutic treatment to the tissue site 5 to which the wound debridement system 1 is applied.

Wound Dressing

In general, the wound dressing 100 includes a wound interface layer 10 configured to provide mechanical movement which disrupts debris 7 at a tissue site 5 and an active layer 40 configured to drive the movement of the wound interface layer 10. An absorbent layer 30 may optionally also be incorporated into the wound dressing 100.

The wound dressing 100 may be substantially planar or may be contoured for application to body surfaces having high curvature. The size of wound dressing 100 can vary depending on the size of the tissue site 5 to be treated. For example, it is contemplated that the size of wound dressing 100 can be within a range of approximately 50 cm$^2$ to approximately 3000 cm$^2$, and more preferably within a range of approximately 300 cm$^2$ to approximately [800 cm$^2$. However, other shapes and sizes of wound dressing 100 are also possible depending on intended use.

i. Wound Interface Layer

The wound interface layer 10 is adapted to contact a tissue site 5 along a lower, wound-facing surface 11 of the wound interface layer 10 to mechanically debride debris 7 at the tissue site 5 upon lateral and/or longitudinal movement of the wound interface layer 10 relative to the tissue site 5. Although the wound interface layer 10 is shown as having a generally rounded rectangular shape, the wound interface layer 10 may be formed having any number of, and combination of, sizes, shapes, and/or thicknesses depending on a variety of factors, such as, e.g. the type of treatment being implemented or the nature and size of the tissue site 5 being treated, etc.

Additionally, the size and shape of the wound interface layer 10 may be selected to accommodate the type of tissue site 5 being treated and the degree of contact (e.g. full or partial contact) desired between the tissue site 5 and the wound interface layer 10. For example, if the tissue site 5 is a wound, the shape, size and thickness of the wound interface layer 10 may vary depending on whether the wound interface layer 10 is intended to partially or completely fill the wound, or if the wound interface layer 10 is intended to only be placed over the wound. If the wound interface layer 10 is intended to partially or completely fill the wound, the size and shape of the wound interface layer 10 may be adapted to the contours of the wound.

Any number of bio-compatible materials may be used to construct the wound interface layer 10. A non-limiting, non-exhaustive list of the various materials that may be used to form the wound interface layer 10 may include: bioresorbable materials; materials configured to serve as a scaffold for new cell-growth, such as, e.g. calcium phosphate, collagen, PLA/PGA, coral hydroxy apatites, carbonates, or processed allograft materials; thermoplastic elastomers; 3D textiles, also referred to as a spacer fabric, such as the 3D textiles produced by Heathcoat Fabrics, Ltd., Baltex, and Mueller Textil Group; foam, such as e.g. GranuFoam®, V.A.C. VeraFlo® foam, or V.A.C. WhiteFoam®, each available from Kinetic Concepts, Inc. of San Antonio, Texas; etc.

The materials used to form the wound interface layer 10, the properties of the wound-facing surface 11 and/or the configuration and structure of the wound-facing surface 11 may be selected to enhance the ability of the wound interface layer 10 to disrupt debris 7 at the tissue site 5. For example, in some embodiments, the wound-facing surface 11 may be formed of an abrasive material. In other embodiments, the wound-facing surface 11 may be defined by a textured surface having an uneven, coarse, or jagged profile that can induce strains and stresses at the tissue site 5. In such embodiments, the wound-facing layer may be formed of an abrasive or non-abrasive material. In yet other embodiments, the wound interface layer 10 may be formed of an abrasive or non-abrasive compressible material, with the compression of the compressible material being adapted to increase the amount by which the wound-facing surface 11 is translated or oscillated laterally and/or longitudinally relative to the tissue site 5 during treatment.

Figure 3:
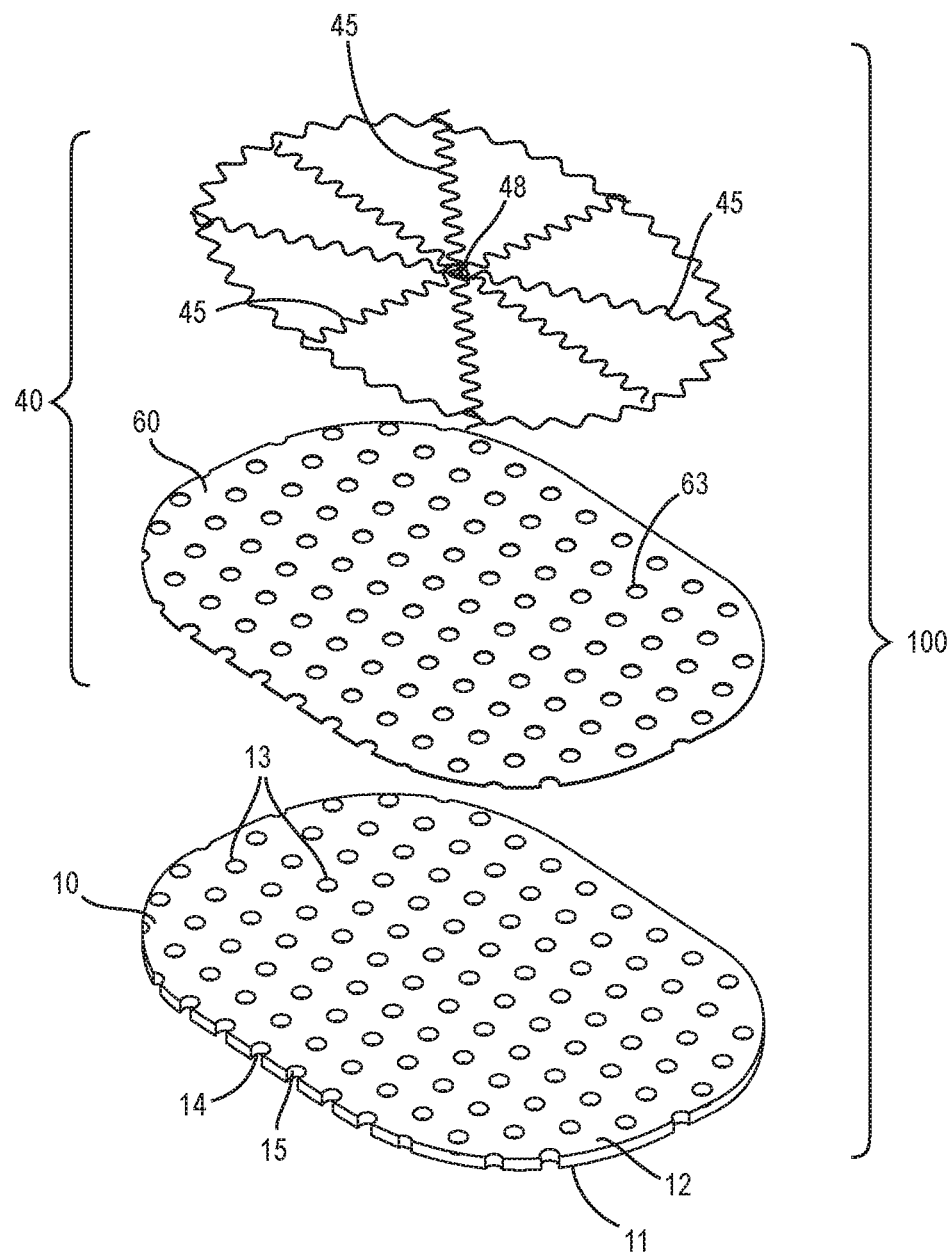
FIG. 3 is an exploded top perspective view of a wound dressing according to an exemplary embodiment.
Figure 4:
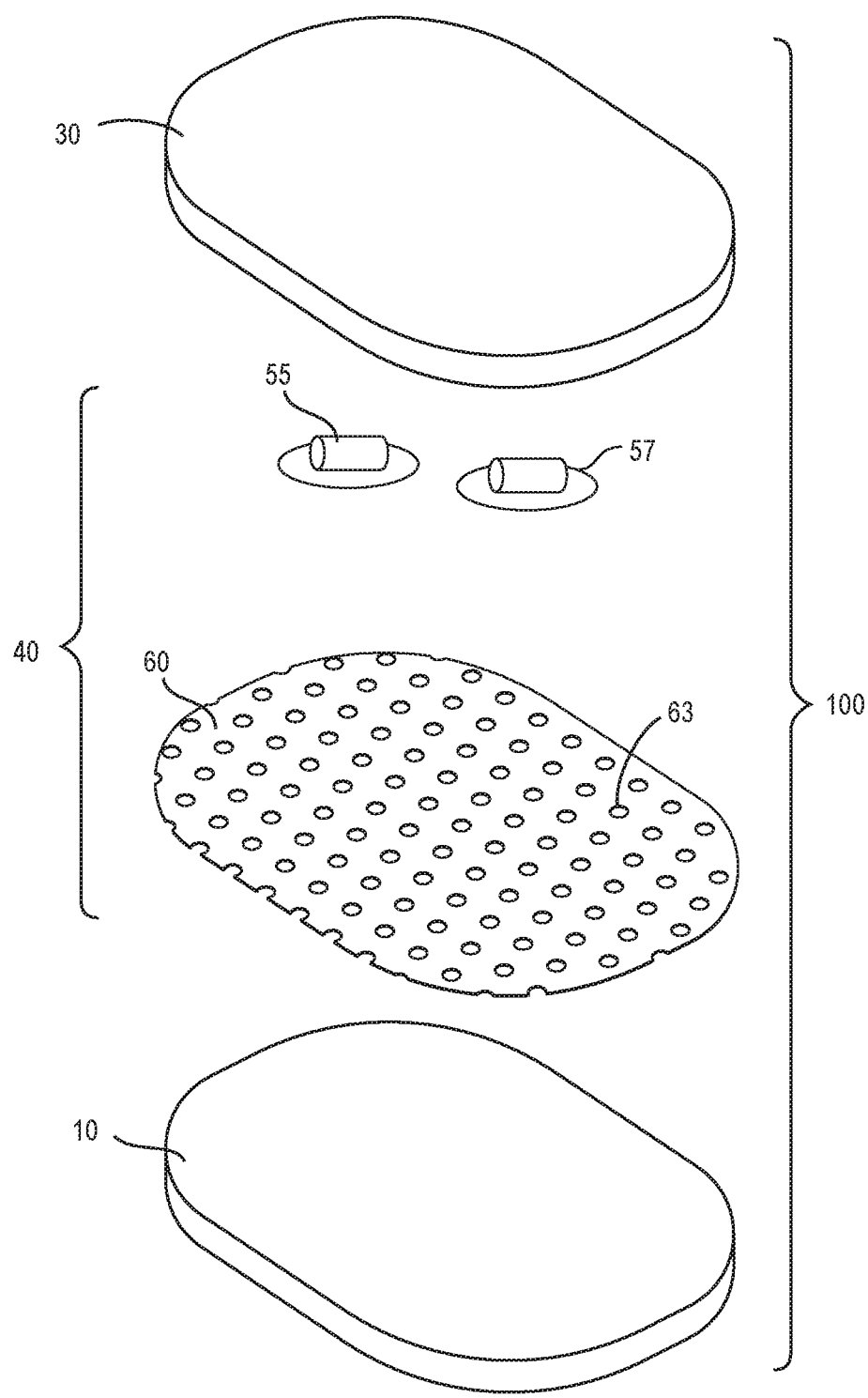
FIG. 4 is an exploded top perspective view of a wound dressing according to an exemplary embodiment.

As illustrated in FIG. 4, in various embodiments the wound-facing surface 11 of wound interface layer 10 may be formed having a generally solid, continuous, uninterrupted surface. In other embodiments, the ability of the wound interface layer 10 to disrupt debris 7 at the tissue site 5 may be enhanced via the selective removal of areas or portions of the wound-facing surface 11. For example, as illustrated in FIG. 3, in one embodiment, the wound interface layer 10 may be constructed with a plurality of perforations or through-holes 13 extending entirely or partially through the wound interface layer 10 from the wound-facing surface 11 to an upper surface 12 of the wound interface layer 10.

The dimensions of the through-holes 13 may be varied as desired. While in some embodiments each of the through-holes 13 may have identical dimensions, in other embodiments the through-holes 13 may be formed having varied dimensions. Regardless of the dimensions selected for the through-holes 13, in embodiments in which the wound interface layer 10 is formed from a foam-like or other porous material, it is to be understood that the through-holes 13 do not include the pores of the material forming the wound interface layer 10, but rather are discrete perforations formed through the material forming the wound interface layer 10.

The through-holes 13 may be arranged about the wound interface layer 10 in any number of desired arrangements or patterns, including a random arrangement of the through-holes 13 about the wound interface layer 10. As illustrated in FIG. 3, in some embodiments, the through-holes 13 may be arranged linearly, with adjacent rows of through-holes 13 optionally being offset from one another.

As shown in FIG. 3, in some embodiments, the through-holes 13 may have a circular shape. In other embodiments, the through-holes 13 may be formed having any number of other shapes, or any combination of different shapes, including, e.g. hexagonal, ovoid, or triangular shapes. When contracted, through-holes 13 having different cross-sectional shapes may generate and distribute concentrated stresses in different dimensions, and may accordingly influence disruption of debris 7 in different ways. As such, in various embodiments the cross-sectional shape of the through-holes 13 may be based on the tissue site 5 being treated and/or the degree of abrasion that may be desired at the tissue site 5.

Regardless of the shape, size, arrangement, or degree to which the through-holes 13 extend through the wound interface layer 10, the through-holes 13 formed in the wound interface layer 10 define void spaces in the wound-facing surface 11. In response to the wound interface layer 10 being compressed, the voids provide spaces into which the wound-facing surface 11 is laterally and/or longitudinally collapsed. As the wound-facing surface 11 is compressed from its initial, relaxed configuration into the spaces defined by the voids, the lateral and/or longitudinal translation of the wound-facing surface 11 relative to the tissue site 5 concentrates a shear force on the tissue site 5 that allows for the disruption of the debris 7 at the tissue site 5.

The disruption of the debris 7 at the tissue site 5 may also be augmented by the localization of forces along the edges 14 of the through-holes 13 during compression of the wound interface layer 10, which may result in the edges 14 acting as cutting surfaces that disrupt debris 7 at the tissue site 5. Additionally, in some embodiments, as a result of the compression of the wound interface layer 10, debris 7 may become trapped within the voids as the through-holes 13 collapse. Forces concentrated by the inner vertical surfaces 15 of the walls of the through-holes 13 on this trapped debris 7 may act to provide additional disruption of the debris 7 at the tissue site 5.

Figure 2:
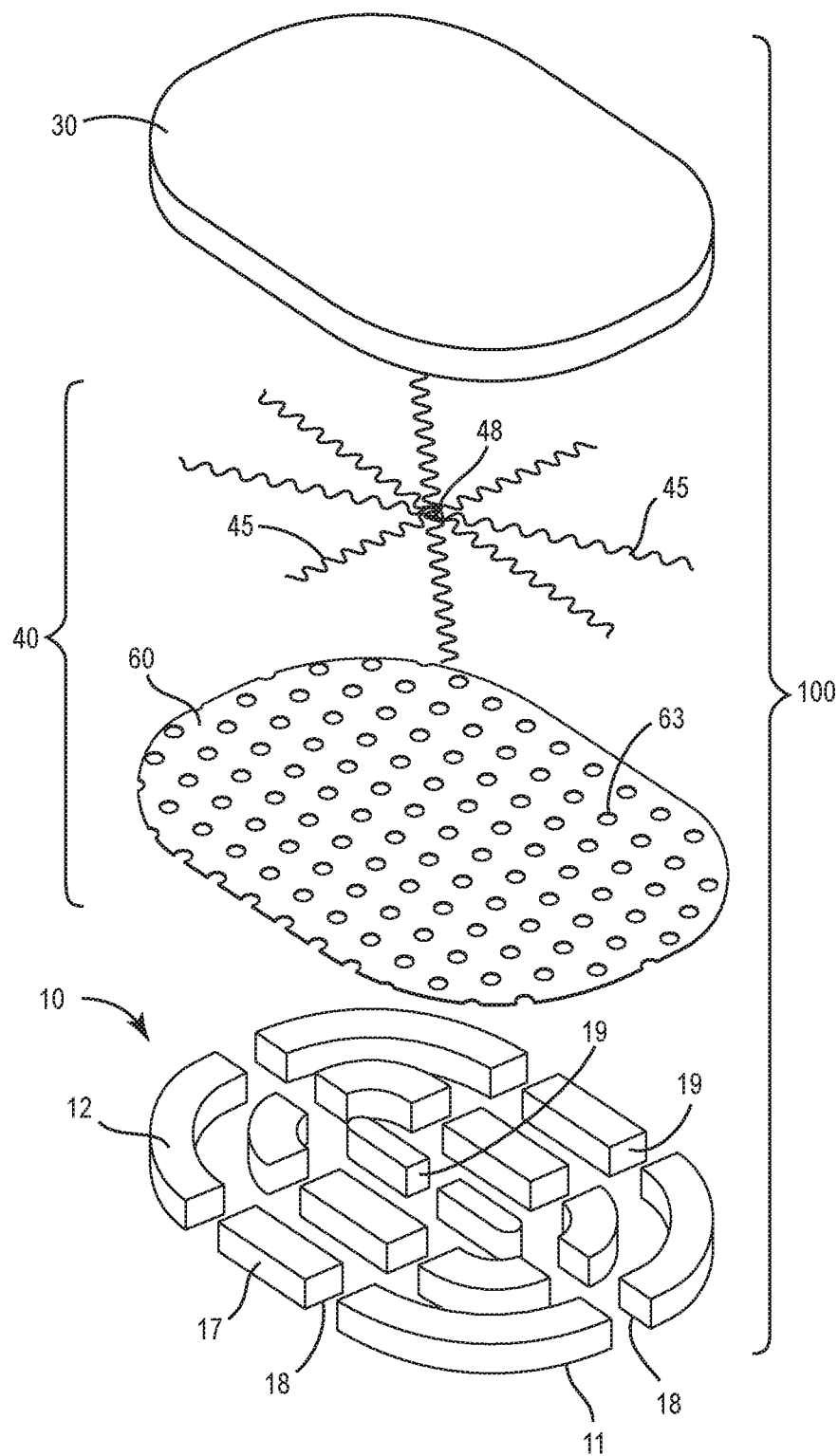
FIG. 2 is an exploded top perspective view of a wound dressing according to an exemplary embodiment.

As illustrated in FIG. 2, in some embodiments, the selective removal of areas or portions of the wound interface layer 10 may be provided in the form of the wound interface layer 10 being formed of a plurality of discrete or connected segments 17. In an initial configuration—prior to the compression of the wound interface layer 10—the segments may be arranged and spaced relative to one another with voids separating adjacent segments 17, such that the wound-facing surface 11 of the wound interface layer 10 is defined by a non-solid, interrupted surface. The segments 17 may be arranged relative to one another such that, upon compression of the wound interface layer 10, the segments 17 collapse inwards to form a substantially solid, compact surface defined by the inter-fitted arrangement of adjacent segments 17 with one another.

The effect of the contraction of the segments 17 of wound interface layer 10 embodiments such as that illustrated in, e.g. FIG. 2, is similar to the effect of the contraction and collapse of through-holes 13 of wound interface layer 10 embodiments such as that illustrated in, e.g. FIG. 3. In particular, the translation of the segments 17 relative to the tissue site 5 concentrates a shear force on the tissue site 5 as the segments 17 are collapsed and translated into the inter-fitted, compressed segment 17 configuration. Also, concentrated forces imparted by the edges 18 of segments 17 on the debris as well as forces imparted by the vertical surfaces 19 of segments 17 on debris 7 that becomes trapped between adjacent segments 17 as the wound interface layer 10 collapses assist in the debridement of debris 7 at the tissue site 5.

Although embodiments of the wound interface layer 10 formed with through-holes 13 or segments 17 each assist in tissue site 5 debridement, in various embodiments, the larger wound-facing surface 11 surface area, the greater amount of defined edges 18, and the greater total surface area defined by vertical surfaces 15 characterizing embodiments of the wound interface layer 10 having segments 17 (such as e.g. illustrated in FIG. 2) may allow for a greater degree of debris 7 disruption as compared to embodiments of the wound interface layer 10 formed with through-holes 13 (such as e.g. illustrated in FIG. 3).

ii. Active Layer

Active layer 40 is configured to intentionally oscillate, translate, collapse, or otherwise move the wound interface layer 10 such that unhealthy tissue or other debris 7 may be debrided from the tissue site 5. The active layer 40 generally comprises one or more drive elements that may be operably coupled to the wound interface layer 10 via a film layer 60 to which the drive elements may be interconnected. Activation of the one or more drive elements causes the movement of the active layer 40, with the movement of the active layer 40 being transferred to the wound interface layer 10 so as to translate the wound-facing surface 11 of the wound interface layer 10 relative to the tissue site 5 and thereby mechanically debride the debris 7 at the tissue site 5.

a. Smart Material Drive Members

Referring to FIGS. 2 and 3, in various embodiments, the drive elements of the active layer 40 may comprise one or more drive members 45 formed of a smart material, with the activation of the drive members 45 by the drive unit 70 being configured to cause the oscillation and transition of the drive members 45 between expanded and collapsed, or between actuated and unactuated, configurations. In turn, the cyclical, alternating, or intermittent movement of the drive members 45 between expanded and collapsed configurations, or between actuated and unactuated states, is configured move the active layer 40, which is then imparted onto the wound interface layer 10 to effectuate lateral and/or longitudinal movement of the wound interface layer 10 relative to the tissue site 5.

For example, in some embodiments, such as, e.g. those illustrated in FIG. 2 or 3, each of the individual drive members 45 of the active layer 40 may be formed of a shape memory alloy, with each of the individual drive members 45 being configured to compress from an initial configuration as shown in FIGS. 2 and 3 to a collapsed configuration (not shown) in response to being exposed to a predetermined activation temperature.

In other embodiments, the drive members 45 of the active layer 40 embodiments illustrated in FIG. 2 or 3 may be formed of an electro-active polymer, with each of the individual drive members 45 forming the active layer 40 being configured to compress from an initial configurations as shown in FIGS. 2 and 3 to a collapsed configuration (not shown) in response to being stimulated by an electric field.

The drive members 45 may be formed of any number of, and any desired combination of known smart materials, including shape memory effect materials such as shape-memory alloys and shape-memory polymers; electro-active polymers; etc. In general, smart materials are materials that are adapted to undergo a change in one or more properties and/or demonstrate a desired effect in response to an external stimulus. For example, smart materials may be configured to change in size or shape when stimulated, or may 'remember' a trained shape to which the material returns to from a deformed configuration when exposed to an external stimulus.

Advantageously, the smart materials that are chosen to form drive members 45 will be selected such that the change(s) the smart material undergoes when exposed to a stimulus will allow for the actuation of the drive members 45 to effectuate the desired movement of the wound interface layer 10. Non-limiting examples of smart materials that may be used to form drive members 45, include, e.g. Cu—Al—Ni alloys; Ni—Ti alloys (e.g. Nitinol); Fe-Me-Si alloys; Cu—Zn—Al alloys; Cu—Al—Ni alloys; thermo-responsive shape-memory polymers; photo-responsive shape-memory polymers; magnetically-responsive shape-memory polymers; chemo-responsive shape-memory polymers; electro-responsive shape-memory polymers; dielectric electroactive polymers; ionic electroactive polymers; etc.

The one or more drive members 45 forming the active layer 40 may be spaced and positioned about the active layer 40 in any desired pattern, design or arrangement. In various embodiments, the configuration of the drive members 45, the materials used to form the drive members 45, and/or arrangement and spacing of the drive members 45 about the active layer 40 may be used as one way to control the rate of oscillation and/or the degree of translation of the wound interface layer 10 relative to the tissue site 5.

For example, in some embodiments, the configuration of the drive members 45, the materials used to form the drive members 45, and/or the arrangement and spacing of the drive members 45 about the active layer 40 may advantageously be varied and selected to maximize the degree by which the active layer 40 can collapse and expand upon activation of the drive members 45. To this effect, in various embodiments, the drive members 45 may be formed having a bellows-like, spring-like, accordion-like or other folded configuration that allows the drive members 45 to transition between a compact and compressed configuration and an elongated and expanded configuration in response to being activated by the drive unit 70.

The pattern, design and arrangement of the drive members 45 about the active layer 40 may be defined by a plurality of individual, discretely positioned drive members 45, or may be defined by a plurality of interconnected individual drive members 45 forming a single, unitary structure having a desired pattern and design, such as, e.g. the hub and spoke pattern illustrated in FIGS. 2 and 3. While in some embodiments the one or more drive members 45 may be arranged uniformly and/or symmetrically about the active layer 40, in other embodiments the drive members 45 may be positioned randomly about the active layer 40.

As shown in FIGS. 2 and 3, in some embodiments, the interconnected, single, unitary structure defined by the plurality of individual drive members 45 may form a spoke-like structure, with individual drive members 45 extending radially outwards from a common central hub 48. As illustrated in FIG. 3, in some embodiments, one or more drive members 45 may additionally extend continuously or interruptedly about a perimeter of the active layer 40, and may optionally be attached to the outwardly located ends of the drive members 45 that define the spoke-like structure. In addition to assisting in the expansion and contraction of the active layer 40, the inclusion of one or more drive members 45 forming an outer ring surrounding the periphery of the hub and spoke assembly may also facilitate the manufacture and assembly of the active layer 40.

In embodiments in which a plurality of individual drive members 45 are interconnected to form a unitary, interconnected structure (such as, e.g. illustrated in FIGS. 2 and 3), the connection of the individual drive members 45 forming the unitary structure may be such that each of the individual drive members 45 forming the unitary structure are operatively connected, with activation of a single drive member 45 forming the interconnected unitary structure being sufficient to activate each of the other drive members 45 forming the interconnected, unitary structure.

Alternatively, in other embodiments in which a plurality of individual drive members 45 are interconnected to form a unitary structure (such as, e.g. illustrated in FIGS. 2 and 3), one or more of the individual drive members 45 may be operatively isolated from the other drive members 45 forming the unitary structure, with the activation of the operatively isolated individual drive member 45 not automatically resulting in the activation of the other drive members 45 forming the unitary structure. In such embodiments, the selective activation of certain operatively isolated, individual drive members 45 may provide control over the degree and/or direction of the lateral and/or longitudinal movement of the wound layer 10 relative to the tissue site 5.

The individual drive members 45 forming the active layer 40 may be adapted to collapse and expand in either single or multiple directions. However, even in embodiments in which the individual drive members 45 forming the active layer 40 are configured to collapse and expand in a single direction, the arrangement and spacing of the drive members 45 about the active layer 40 may be varied so as to achieve either uni- or multi-directional collapse and expansion of the active layer 40. Accordingly, in various embodiments, the drive members 45 may be configured and arranged so as to allow for collapse and expansion of the active layer 40 in one, all, or a combination of the lateral, longitudinal, and/or vertical directions.

For example, as illustrated by the embodiments of FIGS. 2 and 3, in various embodiments, the arrangement of the drive members 45 may be adapted such that activation of the drive members 45 results in the collapse and/or expansion of the drive members 45 inwards/outwards relative to the center of the active layer 40. In other embodiments, the arrangement of the drive members 45 may be varied to achieve collapse and expansion of the active layer 40 in any other desired direction(s).

In various embodiments, the drive members 45 may be formed from smart materials that can be trained to remember and/or be actuated to transition to one or more shapes or configurations, with the drive members 45 being adapted to cyclically, alternatingly, reciprocally, or otherwise intermittently transition to the trained/actuated configuration from an initial configuration (e.g. an unactuated configuration) upon activation of the drive members 45. The cyclical, alternating, reciprocal, or otherwise intermittent transition of the drive members 45 between the first trained/actuated configuration and an initial drive member 45 configuration is configured to result in the oscillation of the active layer 40 by which movement of the wound interface layer 10 is effectuated.

In some embodiments in which the drive members 45 are formed from a smart material that can be trained to remember and/or be actuated to transition to one or more original shapes or configurations, the drive members 45 may be formed from smart materials selected from one-way smart materials, two-way smart materials, and/or multiple-shape smart materials (e.g. three shape/phase) materials. Drive members 45 formed from one-way smart materials may be trained to remember and/or be actuated to a single original shape or configuration, such that, upon activation, the one-way smart material drive members 45 transition from an initial deformed and/or unactuated shape or configuration to their trained and/or actuated configuration. In other embodiments, the drive members 45 may be formed from a two-way smart material that may be trained to remember and/or may be actuated to two distinct shapes or configurations, with the two-way smart material drive members 45 being adapted to allow for a cyclical, reversible transition between the first trained/actuated configuration and the second trained/actuated configuration. In yet other embodiments, the drive members 45 may be formed from multiple-shape smart materials (e.g. three-shape/phase), in which the multiple-shape smart material drive members 45 may be trained to transition and/or be actuated to an intermediate shape as the multiple-shape smart material drive members 45 transition to the trained/actuated configuration in response to being activated.

As will be understood, in various embodiments, the configuration and arrangement of the drive members 45 may be varied depending in part on the type of and properties of the smart materials used to form the drive members 45. For example, in embodiments in which the drive members 45 are formed from a two-way smart material, the drive members 45 may be formed to have a first trained configuration defined by a folded arrangement and a second trained configuration defined by a generally linear arrangement, such that upon a first activation, the drive members 45 transition to the collapsed, first trained/actuated configuration and upon a second activation (or, e.g. a removal of the activation stimulus used to initiate the first transition) the drive members 45 transition to the expanded, second trained/actuated configuration.

In embodiments in which a multiple-shape smart material is used to form drive members 45, the drive members 45 may be trained such that the intermediate and trained configurations correspond to collapsed (e.g. spring-like) and expanded (e.g. linear) shapes, or vice-versa, such that upon activation, the drive members 45 are adapted to cycle between the expanded and collapsed configurations.

In embodiments in which the drive members 45 are formed of a one-way smart material, the spacing and arrangement of the drive members 45, and optionally the incorporation of drive members 45 having different trained/actuated configurations, may be used to effectuate expansion and collapse of the active layer 40. For example, in various embodiments, drive members 45 having opposite trained/actuated configurations (i.e. collapsed and expanded configuration) may be arranged and spaced in a manner about the active layer such that the activation and resultant expansion of a first, initially compressed drive member 45 results in the compression of a second, initially elongated drive member 45, with the subsequent activation of the second drive member 45 causing the elongation of the second drive member 45 and resulting in the compression of the first drive member 45.

Accordingly, although the one-way smart material drive members 45 may each, taken individually, only allow for transition of the one-way smart material drive member 45 to a single collapsed or elongated trained configuration, by varying the spacing, arrangement, and selection of the one-way smart material drive members 45, a continuous, oscillating movement of active layer 40 may be effectuated by the selective activation of the different one-way drive members 45 forming the active layer 40.

b. Oscillating Motor

In some embodiments, the drive element of the active layer 40 may include one or more motors 55 configured to move the wound interface layer 10 laterally and/or longitudinally relative to the tissue site 5. The one or more motors 55 may comprise any number of known motor designs, such as e.g. an oscillating motor, that would provide the desired translational and/or oscillatory movement of the active layer 40.

As illustrated in FIG. 4, the one or more motors 55 may be formed as self-contained modules that are affixed to a semi-rigid support structure 57. While in some embodiments the one or more motors 55 may be attached to the wound interface layer 10 via an intermediate film layer 60 (such as, e.g. shown in FIG. 4), in other embodiments, the support structures 57 and motors 55 may be mounted directly on the wound interface layer 10.

In some embodiments, the operation of the motor 55 may be activated via a control unit 80. In other embodiments, the activation of the motor 55 may alternatively, or additionally, be actuated in response to a pulse of fixed negative or positive pressure being applied to motor 55, either from a direct or indirect source (e.g. pressure being applied directly to the motor 55 or changes in pressure in the ambient environment in which the motor 55 is situated).

For example, in embodiments in which the wound debridement system 1 is used in conjunction with a NPWT system, the application of negative pressure to the wound dressing 100 at the commencement of the NPWT treatment may automatically, indirectly activate the motor 55, such that wound debridement is automatically provided in response to the start of the NPWT treatment without requiring any additional user intervention besides that required to initiate the NPWT treatment.

c. Film Layer

In various embodiments, the active layer 40 may optionally include a film layer 60 to which the drive elements (i.e. drive members 45 and/or motors 55) of the active layer 40 may be mounted, laminated, attached or otherwise interconnected to. Additionally, in various embodiments, the film layer 60 may be used as the basis by which the drive members 45 are affixed to the wound interface layer 10. Alternatively, in some embodiments, the film layer 60 may be omitted from active layer 40, with the drive elements of the active layer 40 being attached directly to the wound interface layer 10.

The size and shape of the film layer 60 may be varied as desired. In various embodiments, the outer periphery of the film layer 60 may be shaped and sized to generally correspond to, or optionally be smaller than, the outer periphery of the wound interface layer 10.

The film layer 60 may be adapted to elastically deform upon application of a stretching force to the wound dressing 100. For example, in some embodiments, the film layer 60 may be designed to elastically stretch when a stretching force is applied and elastically recover when the stretching force is removed, such as, e.g. may occur as a result of the collapse and expansion of the drive members 45 that are supported by film layer 60. In other words, film layer 60 may be configured to exhibit substantially elastic deformation and recovery.

Film layer 60 may be a thin layer made of any number of elastic materials. For example, film layer 60 may be a polyurethane film, a polyethylene film, or other thin elastic. In some embodiments, film layer 60 may be substantially impermeable to liquid and substantially permeable to moisture vapor.

In embodiments in which the wound debridement system 1 will be used with additional therapeutic treatments, such as, e.g. NPWT or instillation therapy, film layer 60 may optionally include one or more fenestrations 63 adapted to allow for the transfer of fluids and pressure to/from the wound interface layer 10. The fenestrations 63 may also be adapted to reduce the amount of force required to stretch film layer 60.

In some embodiments, such as illustrated, e.g. in FIG. 1, film layer 60 may comprise an upper film 61 and a lower film 62 that encapsulate the drive element (e.g. drive members 45 and/or motor 55). In some such embodiments, one or both of the upper film 61 and the lower film 62 may include fenestrations 63.

In other dual-film film layer 60 embodiments, both the upper film 61 and the lower film 62 may be formed without fenestrations 63, with the edges of the upper film 61 and lower film 62 being attached together to form a fluid-tight seal that isolates the interior 66 of the film layer 60 from the external environment. In such embodiments, the film layer 60 may comprise one or more outlets, such as e.g. a port 67, by which fluid communication may be established between the film layer 60 interior 66 and the external environment.

iii. Absorbent Layer

An absorbent layer 30 may optionally be coupled to the active layer 40 opposite the wound interface layer 10, such that the active layer 40 is encapsulated between the absorbent layer 30 and the wound interface layer 10. The absorbent layer 30 may act as a manifold that is adapted to collect and/or distribute fluid and/or pressure across a tissue site 5. For example, the absorbent layer 30 may be adapted to receive and distribute negative pressure across a tissue site 5 to which the wound dressing 100 is applied, allowing for the wicking of fluid (e.g. exudate) from the tissue site 5 and providing a distributed compressive force along the tissue site 5. As another example, the absorbent layer 30 may be used to facilitate the delivery of fluid across a tissue site 5.

In embodiments incorporating an absorbent layer 30, the size and shape of the absorbent layer 30 may be varied as desired. In various embodiments, the outer periphery of the absorbent layer 30 may be shaped and sized to generally correspond to, or optionally be smaller than, the outer periphery of the wound interface layer 10.

Any material or combination of materials might be used for the absorbent layer 30. In some embodiments, the absorbent layer 30 may comprise a porous and permeable foam layer, with the absorbent layer 30 being formed from a reticulated, open-cell polyurethane or polyether foam that allows good permeability of wound fluids while under a reduced pressure. In one non-limiting example, the absorbent layer 30 may be an open-cell, reticulated polyurethane foam such as GranuFoam® dressing available from Kinetic Concepts, Inc. of San Antonio, Tex. In other embodiments the absorbent layer 30 may be an open-cell, reticulated polyurethane foam such as a V.A.C. VeraFlo® foam, also available from Kinetic Concepts, Inc., of San Antonio, Tex. In yet other embodiments, the absorbent layer 30 may be formed of un-reticulated open-cell foam.

Drape Layer

A drape layer 20 adapted to seal to a patient's skin 3 may advantageously be provided to position and maintain the active debridement wound dressing 100 about the desired treatment tissue site 5. An attachment device, such as e.g. an adhesively coated margin 23, as illustrated e.g. in FIG. 1 may be used to attach the drape layer 20 to a desired location along the patient's skin 3. In various embodiments, the drape layer 20 may provide a bacterial barrier and protection from physical trauma, and may be permeable to water vapor but impermeable to liquid.

Drape layer 20 may be formed from any number of materials, such as, e.g. polyurethane film. In some embodiments, the drape 20 may be adapted to provide a fluid-tight seal with the patient's skin 3 surrounding the tissue site 5 that is to be treated. In such embodiments, the drape layer 20 may be constructed from a material adapted to reduce evaporative losses and provide and maintain a fluid seal. As non-limiting examples, the drape layer 20 may be formed from materials that include a silicone, 3M Tegaderm® drape material, acrylic drape material such as one available from Avery, or an incise drape material.

Drive Unit

The drive unit 70 of the wound debridement system 1 is configured to activate the drive element(s) (i.e. drive members 45 and/or motors 55) to effectuate lateral and/or longitudinal movement of the wound interface layer 10 relative to the tissue site 5. In some embodiments, the drive unit 70 may be provided on or within the drape layer 20 and/or wound dressing 100, while in other embodiments the drive unit 70 may be provided remote from the drape layer 20 and/or wound dressing 100.

i. Drive Member Drive Unit

Any number of drive unit 70 configurations may be used to provide the desired activation of the drive members 45, with the configuration and operation of the drive unit 70 being selectable based on any number of factors, such as, e.g., the threshold activation properties of the smart material used to form the drive members 45 (e.g. whether the smart material is thermally, electrically, chemical, magnetically, activated, etc.), the type of smart material used to form the drive members, and/or whether additional therapeutic treatment system(s) are being used in conjunction with the wound debridement system 1, etc.

In active layer 40 embodiments in which the smart material forming the drive members 45 is thermally activated and the activation temperature of the drive members 45 is above room temperature (e.g. activation temperatures that are above approximately 60° F.) and below body temperature (e.g. activation temperatures that are below approximately 80° F.), it may not be necessary that the wound debridement system 1 include a drive unit 70, as the heat emanating from the tissue site 5 at which the wound dressing 100 is positioned may be sufficient to activate the active layer 40.

However, in other embodiments, or, e.g. when the drive members 45 are thermally activated at a temperature that is above body temperature (e.g. activation temperatures that are above approximately 90° F.) or below room temperature (e.g. activation temperatures that are below approximately 70° F.), a drive unit 70 may be provided to warm or cool the drive members 45 to the activation temperature using a warmed or cooled fluid. In such embodiments, the warming/cooling fluid may be delivered in any number of ways to heat/cool the drive members 45 to the requisite activation temperature.

For example, when the wound debridement device 1 is used in conjunction with an installation therapy system (such as e.g. a V.A.C. VERAFLO™ therapy system as available from Kinetic Concepts, Inc. (KCI) of San Antonio, Tex.), the drive unit 70 may be configured to heat/cool the instillation therapy fluid to the desired activation temperature prior to the instillation fluid being delivered to the tissue site 5. In such embodiments, drive unit 70 may be incorporated into the instillation therapy system fluid delivery component, and the conduit 75 and port 67 provided on the drape layer 20 may be comprised of portions of the instillation therapy system by which the installation fluid is provided by the fluid delivery component of the instillation therapy device to a treatment space 25 surrounding the tissue site 5 defined by the patient's skin 3 and the drape layer 20.

However, in some embodiments, the activation temperature of the drive members 45 may be too high or too low for a warmed/cooled fluid to be applied directly to the tissue site 5; the duration of the instillation therapy may be too short for the drive members 45 to be activated by the warmed/cooled instillation fluid; and/or the warming/cooling of the instillation fluid may not be possible (e.g. because of an adverse therapeutic effect of heating/cooling on the instillation fluid).

Accordingly, in some embodiments, it may be desirable to isolate the delivery of the fluid to the active layer 40. As illustrated in FIG. 5, in such embodiments, the drive members 45 may be encapsulated within the interior 66 of a non-fenestrated film layer 60, with one or more ports 67 formed in the film layer 60 allowing for the warmed/cooled fluid to be provided to, and optionally removed from, the active layer 40. In such embodiments, the warming/cooling fluid may comprises any desired fluid, such as, e.g. saline.

As will be understood, such drive unit 70 embodiments as described with reference to activation via a warmed/cooled fluid may also be utilized in embodiments in which the drive members 45 are chemically activated.

In other embodiments, activation of the drive members 45 may be triggered by the application of electrical current to the active layer 40. Such embodiments may be advantageous for embodiments in which the drive members 45 have high or low activation temperatures (as in such embodiments it may not be desirable to supply a warmed/cooled fluid having such a high/low temperature in the vicinity of the tissue site 5) and/or in embodiments in which the drive members 45 are formed from an electro-active polymer material. In such embodiments, the drive unit 70 may be configured to provide current to the active layer 40 so as to actuate the drive members 45.

In embodiments in which the wound debridement system 1 is used in conjunction with an additional therapeutic treatments system, the source of current may optionally be provided by a component of the additional therapeutic treatment system. For example, in some embodiments, the wound debridement system 1 may be used in conjunction with a V.A.C. VERAFLO™ therapy system as available from Kinetic Concepts, Inc. (KCI) of San Antonio, Tex., with the source of current used to activate the drive members 45 being provided by the V.A.C. ULTA™ component of the system.

In such embodiments, a wire (not shown) may be provided through a conduit 75 extending between the drive unit 70 (or component of the additional therapeutic treatment system, such as, e.g. ULTA™ component) and the active layer 40, by which current from the drive unit 70 is provided to the active layer 40.

As will be understood, the drive unit 70 embodiments described above are only exemplary embodiments, and are not intended to limit the type of and/or configuration of the drive unit 70 that may be used to activate the drive members 45. As further non-limiting examples, in other embodiments the drive unit 70 may be configured to activate the drive members 45 using light (either directly or as a heat source) or magnetic fields.

As explained above, in some embodiments, the active layer 40 may comprise drive members 45 formed of different types of materials having different activation thresholds and/or the materials may be formed having multiple trained configurations that are activated at different threshold levels. Accordingly, it is also to be understood that, in various embodiments, the drive unit 70 may be adapted to allow for activation at one or more threshold levels (e.g. the drive unit may be configured to allow for delivery of fluids at different temperatures, or apply varying electric current, etc.) as required to drive the drive members 45 so as to be able to achieve a continuous, oscillating movement of the wound interface layer relative to the tissue site 5.

Additionally, as also explained above, in some embodiments, one or more of the plurality of drive members 45 may be operatively isolated from other drive members 45, with the arrangement and spacing of the drive members 45 about the active layer 40 being such that selective activation of one or more of the operatively isolated drive members 45 is adapted to control the movement of the active layer 40.

Accordingly, in some embodiments, the drive unit 70 may also be adapted to allow for the selective activation of individual drive members 45.

For example, in one embodiment (not shown), the active layer 40 may comprise a plurality of laterally extending drive members 45 and a plurality of longitudinally extending drive members 45 that form a grid-like pattern, with the plurality of laterally extending drive members 45 being operatively isolated from the plurality of longitudinally extending drive members 45. In such an embodiment, the drive unit 70 may be operably connected to at least one of the laterally extending drive members 45 and at least one of the longitudinally extending drive members 45, such that by selectively activating the laterally and/or longitudinally extending drive members 45, the drive unit 70 may allow for both lateral and longitudinal translation of the wound interface layer 10 relative to the tissue site 5.

ii. Oscillating Motor Drive Unit

In active layer 40 embodiments in which the driving element is a motor 55, the drive unit 70 may, in various embodiments, be provided within the self-contained module defining the motor 55, such as, e.g. illustrated in FIG. 4. Alternatively, as illustrated in FIGS. 1 and 5, in other embodiments, the drive unit 70 may be provided remote from the self-contained module defining the motor 55, and may instead be provided on or within the wound dressing 100 and/or drape layer 20, such as, e.g. illustrated in FIG. 1, or remote from the wound dressing 100 and/or drape layer 20, such as, e.g. illustrated in FIG. 5. In various embodiments, the drive unit 70 for the motor 55 comprises a power source configured to supply an electric current to drive the motor 55.

Control Unit

The activation of the active layer 40 may be based upon signals received from an optionally included control unit 80 adapted to control the operation of the drive unit 70 in activating the drive elements of the active layer 40. In some embodiments, the control unit 80 and drive unit 70 may be formed as a single unit, while in other embodiments the drive unit 70 and control unit 80 may be provided separately. The communication between the control unit 80 and the drive unit may be accomplished using any number of known communication methods, including wireless communication.

As will be understood, in addition to simply starting and stopping the movement of the active layer 40, the control unit 80 may also be adapted to allow for the adjustment and variation of the movement of the active layer 40. The control unit 80 may be adapted to vary the operation of the drive unit 70 based on any number of factors including, but not limited to: the tissue site 5 being treated (such as, but not limited to bone tissue, adipose tissue, muscle tissue, neural tissue, dermal tissue, vascular tissue, connective tissue, cartilage, tendons, or ligaments, chronic, acute, traumatic, subacute, and dehisced wounds, partial-thickness burns, ulcers, flaps, grafts, etc.); the type of debris 7 being debrided (such as, but not limited to necrotic tissue, eschar, impaired tissue, other sources of infection, exudate, slough including hyperkeratosis, pus, foreign bodies, biofilm, or other types of bioburden, etc.); the thickness, consistency, color and/or moisture levels of the debris 7; the desired relative amount of movement of the wound interface layer 10 relative to the tissue site 5; etc.

Standalone Use and Use with Other Treatment Systems

In various embodiments, wound debridement system 1 may be used as a standalone therapy device, with drive unit 70 and optional control unit 80 being provided solely for the operation of the wound debridement system 1. However, as noted previously, in other embodiments it may be possible to utilize the wound debridement system 1 in conjunction with one or more additional therapeutic treatment systems configured to provide a desired therapeutic treatment to the tissue site 5 in addition to the debris 7 debridement provided by the wound debridement system 1.

Referring to FIG. 1, in some embodiments, wound debridement system 1 may be provided as a substantially self-contained system. As shown in FIG. 1, drape layer 20 may be used to secure the wound dressing 100 to the patient's skin 3 at a location surrounding the targeted tissue site 5. A remote control unit 80 may optionally be provided, and may allow for wired or wireless activation of the active layer 40. In some embodiments, a drive unit 70 may be provided on or within the drape layer 20.

Depending on the mechanism by which the drive unit 70 activates the drive elements of the active layer 40, a conduit 77 may optionally extend between the drive unit 70 and the active layer 40. As will be understood, in embodiments in which the active layer 40 comprises a motor 55 defined by a self-contained module housing the drive unit 70, the drive unit 70 depicted in FIG. 1 may optionally be omitted from the wound debridement system 1 of FIG. 1.

Although, as illustrated in FIG. 1, in some embodiments the drive unit 70 may be provide on or within the drape layer 20, in other embodiments it may not be desirable to provide or assemble the drape layer 20/wound dressing 100 and the drive unit 70 as a single unit. Accordingly, as illustrated in FIG. 5, in various embodiments, drive unit 70 may be provided separate from the drape layer 20 and wound dressing 100.

As shown in FIG. 5, in such embodiments, drape layer 20 may include a port 27 (such as, e.g. a SENSAT.R.A.C™ port as available from Kinetic Concepts, Inc. (KCI) of San Antonio, Tex.) that is used to operatively connect the wound dressing 100 and drape layer 20 to the drive unit via a conduit 75. Depending on the mechanism by which the drive unit 70 is configured to activate the active layer 40, the conduit 75 maybe in communication with the interior space 25 defined between the drape layer 20 and the patients' skin 3 and/or may extend to a port 67 provided on the film layer 60 (as shown in dashed lines).

Although the wound debridement system 1 may be used as a standalone treatment device, in some embodiments the wound debridement system 1 may be used in conjunction with one or more additional therapeutic treatment systems. In such embodiments, one or more of the components of the wound debridement system 1 may optionally comprise one or more elements of the additional therapeutic treatment system. For example, in embodiments in which the wound debridement system 1 is used in conjunction with an additional therapeutic treatment system incorporating a backing layer to position and maintain an element of the additional therapeutic treatment system against a patient's skin 3 during therapy, the drape layer 20 may comprise the backing layer of the additional therapeutic treatment system.

In various embodiments, the additional therapeutic treatment system that the wound debridement system 1 is used in conjunction with may be a NPWT system. The use of the wound debridement system 1 with the NPWT system may improve the functioning of both systems, as the debridement of the debris 7 at the tissue site 5 may improve the efficacy of the NPWT treatment, while the negative pressure applied by the NPWT system may advantageously assist in removing the debris 7 that has been loosened and removed from the tissue site 5 by the wound debridement system 1.

Because the drive elements (i.e. the drive members 45 and the motor 55) of the active layer 40 described herein are not pneumatically driven, the wound dressing 100 of the wound debridement system 1 may be operated simultaneously with the NPWT treatment without the risk of interfering with the continuous negative pressure that is applied during NPWT treatment.

In some embodiments, the wound debridement system 1 may be used in conjunction with an instillation therapy system. In such embodiments, a NPWT system may also optionally be included. The instillation therapy system may assist in the hydration and flushing of the tissue site 5, which may facilitate the debridement of the debris 7 by the wound debridement system 1. In turn, the wound debridement system 1 may allow for greater control of the instillation therapy system.

More specifically, in some embodiments, the active layer 40 may be actuated by the drive unit 70 during the instillation fill, soak and removal phases of instillation therapy. During the fill phase, the actuation of the active layer 40 may encourage a thorough and uniform distribution of the instillation fluid at the tissue site 5 by the wound interface layer 10. During the soak phase, the hydrating effect of the instillation fluid at the tissue site 5 may increase the debridement efficiency of wound interface layer 10. Additionally, in some embodiments, the instillation fluid may optionally contain a topical solution that may assist in reducing patient discomfort during the debridement process. Finally, the flushing and fluid removal phase of the instillation therapy may encourage and assist in the removal of debrided debris 7 from the tissue site 5.

In some embodiments, the wound debridement system 1 may be used in conjunction with (either before, during or after) existing tissue removal and debridement systems and methods. For example, the wound debridement system 1 may be used prior to enzymatic debridement to soften the debris 7. In another example, an existing mechanical debridement technique or method may be used to remove a portion of the debris 7 at the tissue site 5, and the wound debridement system 1 may then be used to remove the remaining debris 7 while reducing the risk of trauma to the tissue site 5.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

We claim:

1. An active debridement wound dressing comprising:
   a wound interface layer comprising an abrasive surface configured to contact a wound and mechanically debride the wound when the wound interface layer moves relative to the wound;
   an active layer coupled to the wound interface layer and comprising a shape memory alloy configured to expand or contract when activated, thereby causing the wound interface layer to move relative to the wound and mechanically debride the wound; and
   a foam layer coupled to the active layer opposite the wound interface layer such that the active layer is encapsulated between the foam layer and the wound interface layer.

2. The active debridement wound dressing of claim 1, wherein:
   the active layer comprises a fenestrated film fixed to the wound interface layer; and
   the shape memory alloy comprises a plurality of segments of the shape memory alloy fixed to the fenestrated film.

3. The active debridement wound dressing of claim 1, wherein the active layer comprises:
   a central hub of the shape memory alloy; and
   a plurality of radial segments of the shape memory alloy extending radially outward from the central hub.

4. The active debridement wound dressing of claim 3, wherein the active layer comprises a perimeter of the shape memory alloy forming a closed shape around the central hub and the plurality of radial segments.

5. The active debridement wound dressing of claim 1, wherein the shape memory alloy is activated by electric current and configured to expand or contract when the electric current is applied to the shape memory alloy.

6. The active debridement wound dressing of claim 1, wherein the shape memory alloy is activated by light to expand or contract when one or more wavelengths of light are applied to the shape memory alloy.

7. The active debridement wound dressing of claim 1, wherein the shape memory alloy is activated by temperature and configured to expand or contract when a temperature of the shape memory alloy reaches an activation temperature.

8. The active debridement wound dressing of claim 1, further comprising a control unit coupled to the active layer and configured to activate the active layer by applying at least one of an electric current, a temperature, or light to the active layer.

9. The active debridement wound dressing of claim 1, wherein the shape memory alloy is configured to forcefully return to a non-activated size or shape when no longer activated.

10. The active debridement wound dressing of claim 9, wherein the shape memory alloy is configured to oscillate between the non-activated size or shape and an activated size or shape to impart oscillating movement to the wound interface layer.

* * * * *